United States Patent
Cantor et al.

(10) Patent No.: US 6,776,989 B2
(45) Date of Patent: Aug. 17, 2004

(54) INTRATRACHEAL ADMINISTRATION OF LYSOZYME

(76) Inventors: Jerome Owen Cantor, 12-15 Estates La., Bayside, NY (US) 11360; Bronislava Shteyngart, 242 92nd St. (2nd Flr.), Brooklyn, NY (US) 11209

( * ) Notice: Subject to any disclaimer, the term of this patent is extended or adjusted under 35 U.S.C. 154(b) by 0 days.

(21) Appl. No.: 09/826,731

(22) Filed: Apr. 5, 2001

(65) Prior Publication Data

US 2001/0036443 A1 Nov. 1, 2001

Related U.S. Application Data

(60) Provisional application No. 60/195,315, filed on Apr. 10, 2000.

(51) Int. Cl.[7] ........................ A61K 38/47; A01N 25/02; C12N 9/36
(52) U.S. Cl. ........................ 424/94.61; 435/206; 424/43
(58) Field of Search ................................ 424/94.61, 43; 435/206

(56) References Cited

U.S. PATENT DOCUMENTS 5,993,809 A * 11/1999 Weaver et al.

OTHER PUBLICATIONS

Luniakin et al., Pediatriia, Akusherstvo, I Ginekolgiia, Jan.–Feb. 1977 (1), 11–13. "Lysozyme in the overall treatment of children with influenza infection and pneumonia".*

Vyrenkov et al., Antibiotiki, 1982, 27(6), 440–447.*

Gavrilenko et al. The Characteristics of lysozyme and carbenicillin action on the clinico–immunological status of patients with chronic bronchitis. Lik Sprava, 1992, Aug;(8):42–45, abstract.

Kats et al. Prevention and treatment of early post–intubation complications using lysozyme. Anesteziol Reanimatol, 1986, May–Jun.; (3):61–2, abstract.

Zhorov et al. Prevention of early post–intubation complications. Eksp Khir Anesteziol, 1971, Jan.–Feb.; 16(1):58–62, abstract.

* cited by examiner

*Primary Examiner*—Michael Meller

(57) ABSTRACT

The subject invention is directed to the treatment of respiratory disorders by intratracheal administration of an effective amount of lysozyme. Respiratory disorders include emphysema, pneumonia, respiratory distress syndrome, bronchopulmonary dysplasia, interstitial fibrosis, cystic fibrosis, and neoplasia. The treatment is intended for a variety of animals, such as premature neonates to adult humans. Administration of lysozyme may be performed by aerosol, which can be generated by a nebulizer or by instillation. The lysozyme may be administered alone or with a carrier such as saline solution, DMSO, and alcohol, or water. It may also be used as a vehicle for the intratracheal administration of drugs or other agents to the lung. The lysozyme may be isolated from a natural source, such as eggs, or synthesized by a bioprocess, such as fermentation. The effective daily amount of lysozyme is from about 10 $\mu$g/kg to about 1 mg/kg of body weight.

8 Claims, 6 Drawing Sheets

30 min 24 hrs

INTRATRACHEAL ADMINISTRATION OF LYSOZYME

This application claims the benefit of Provisional Application No. 60/195,315 filed Apr. 10, 2000.

BACKGROUND OF THE INVENTION

Lysozyme is increased in inflammatory reactions and is a component of the extracellular matrix, but its possible role in lung diseases such as emphysema and interstitial fibrosis has not been investigated. Determining the significance of any changes in pulmonary lysozyme content is complicated by the fact that this protein has no recognized physiological function in the lung other than protecting it from bacterial infection (1–3).

To further understand the role of lysozyme in pulmonary disease, tissue sections from normal, fibrotic, and emphysematous human lungs were evaluated for differences in lysozyme content. An increase in extracellular lysozyme was specifically observed in lung tissues with pulmonary emphysema, and the protein was preferentially associated with elastic fibers, which undergo breakdown in this disease (4).

Since this laboratory and other investigators have previously shown that hyaluronan and other polysaccharides surround elastic fibers (5–7), normal lung tissues were treated with hyaluronidase and examined for their ability to bind exogenously administered lysozyme. Such treatment resulted in increased attachment of lysozyme (4), suggesting that degradation of extracellular matrix components, as occurs in pulmonary emphysema, may expose binding sites for lysozyme on elastic fibers. In vitro studies, using an extracellular matrix preparation mainly composed of elastic fibers, confirmed that lysozyme has a strong affinity for these fibers (unpublished observations).

While the mechanism responsible for the observed affinity of lysozyme for elastic fibers is unclear, it is possible that lysozyme may bind to specific carbohydrate residues in elastic fibers. N-acetyl-D-glucosamine, a component of bacterial cells susceptible to degradation by lysozyme, has also been found in glycoproteins associated with elastic fibers (8). Injury to elastic fibers, as occurs in pulmonary emphysema, may expose such residues, thereby facilitating lysozyme binding.

The enhanced binding of lysozyme to elastic fibers in pulmonary emphysema may protect these fibers from further injury. Previous work by other investigators has shown that lysozyme prevents elastolysis in vitro (9). Lysozyme could therefore be useful in treating emphysema and other diseases involving damage to elastic fibers, such as asthma, pulmonary fibrosis, respiratory distress syndrome, bronchopulmonary dysplasia, and cystic fibrosis. This protective effect of lysozyme would complement its antibacterial properties (1–3) and make it particularly beneficial in the treatment of certain types of pulmonary infections where there is necrotizing lung injury. Similarly, lysozyme has been reported to counteract HIV infection (10) and may therefore be useful in the treatment of pneumonias and other disorders associated with AIDS.

Another useful property of lysozyme is its ability to bind to and disaggregate hyaluronan and other polyanionic compounds (11). Lysozyme might therefore be utilized to treat lung diseases involving excess mucus secretion in airways. In particular, this protein may help alleviate the obstruction of airways associated with pneumonias, asthma, and cystic fibrosis.

This same ability of lysozyme to disaggregate hyaluronan may also be beneficial in pulmonary fibrosis, where significant accumulation of this polysaccharide occurs in conjunction with collagen, elastin and other polysaccharides (12–14). By disaggregating hyaluronan, lysozyme may interfere with the fibrotic process, thereby ameliorating the disease. As shown in studies from this laboratory (4), there is a decrease in lung lysozyme content in pulmonary fibrosis (relative to the proliferation of other tissue components), which may conceivably facilitate the fibrotic response.

With regard to intratracheal administration of lysozyme, this laboratory has shown that an aerosol preparation of the protein rapidly penetrates the lung, remains there for at least 24 hrs, and does not cause pulmonary injury (unpublished observations). These findings suggest that lysozyme could also act as a vehicle for intratracheal delivery of drugs for the treatment of pulmonary and systemic diseases. By virtue of its attachment to elastic fibers, lysozyme could slow the pulmonary clearance of inhaled therapeutic agents, thereby increasing their effectiveness in the lung.

SUMMARY OF THE INVENTION

The subject invention is directed to the treatment of respiratory disorders by intratracheal administration of an effective amount of lysozyme. Respiratory disorders include emphysema, pneumonia, respiratory distress syndrome, bronchopulmonary dysplasia, interstitial fibrosis, cystic fibrosis, and neoplasia. The treatment is intended for a variety of mammals, such as premature neonates to adult humans.

Administration of lysozyme may be performed by aerosol, which can be generated by a nebulizer, or by instillation. The lysozyme may be administered alone, or with a carrier such as saline solution, DMSO, an alcohol, or water. It may also be used as a vehicle for the intratracheal administration of drugs or other agents to the lung. The lysozyme may be isolated from a natural source, such as eggs, or synthesized by a bioprocess, such as fermentation. The effective daily amount of lysozyme is from about 10 $\mu$g/kg to about 1 mg/kg of body weight.

Figure 1:
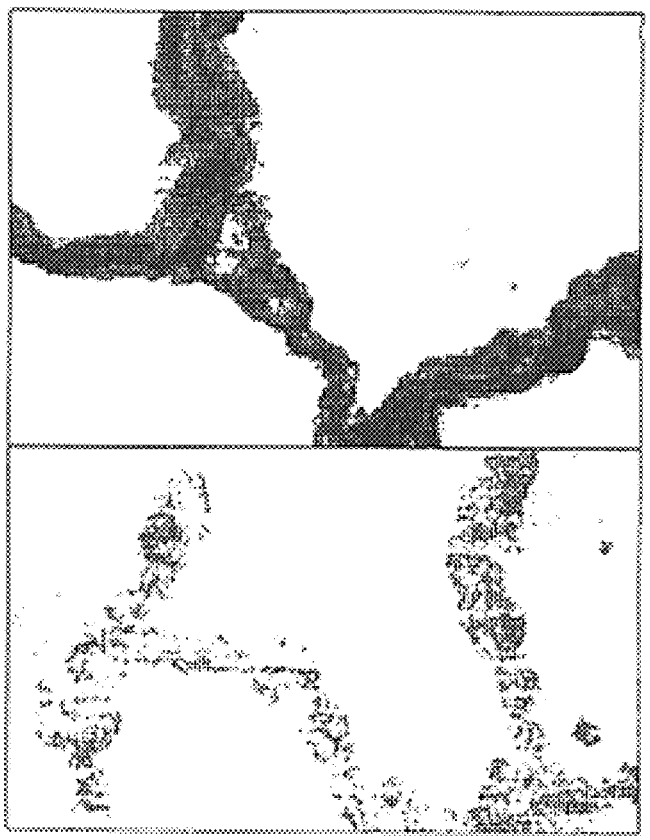
FIG. 1.

Immunostaining for lysozyme was significantly increased in pulmonary emphysema compared to normal lungs.

FIG. 2:

Disrupted elastic fibers in emphysematous lungs showed prominent immunostaining for lysozyme (Avidin-biotin labeling counterstained with Mayer's hematoxylin. Original magnification: ×2000).

FIG. 3:

Immunofluorescence studies with anti-lysozyme antibodies, performed after treatment of the matrix with lysozyme, produced a pattern that resembled the appearance of matrix elastic fibers. The finding indicates that lysozyme binds to these fibers.

FIG. 4:

Treatment of radiolabeled matrix with lysozyme produced no significant release of radioactivity, indicating that the protein does not cause elastolysis.

FIG. 5:

Photomicrograph of lung, 24 hrs after exposure to aerosolized lysozyme. No inflammatory changes, such as alveolitis or interstitial edema, are present.

FIG. 6:

Immunofluorescence studies, using anti-lysozyme antibodies, demonstrated that the exogenous lysozyme was present in the pulmonary interstitium 30 minutes after completion of the aerosol exposure and could still be detected at 24 hrs.

DETAILED DESCRIPTION OF THE INVENTION

The subject invention is directed to the treatment of respiratory disorders by intratracheal administration of an effective amount of lysozyme. Respiratory disorders include pulmonary emphysema, pneumonia, respiratory distress syndrome, bronchopulmonary dysplasia, interstitial fibrosis, cystic fibrosis, and neoplasia. The treatment is intended for a variety of mammals, such as premature neonates to adult humans.

Administration of lysozyme may be performed by aerosol, which can be generated by a nebulizer, or by instillation. The lysozyme may be administered alone, or with a carrier such as saline solution, DMSO, an alcohol, or water. It may also be used as a vehicle for the intratracheal administration of various agents, such as those, which prevent degradation of elastic fibers or promote their resynthesis. The lysozyme may be isolated from a natural source, such as eggs, or synthesized by a bioprocess, such as fermentation. The effective daily amount of lysozyme is from about 10 µg/kg to about 1 mg/kg of body weight.

The amount of lysozyme intratracheally administered daily to a human being may vary from about 10 µg/kg to about 1 mg/kg of body weight. Preferably, the daily amount is from about 10 µg/kg to about 100 µg/kg, for example about 50 µg/kg body weight of the human being treated (daily). The intratracheal lysozyme may be administered in any of the methods well known to those skilled in the art. For example, the lysozyme may be administered in the form of an aerosol or may be administered by instillation. If administered in the form of an aerosol, a nebulizer is used to produce lysozyme in aerosol form (See for example U.S. Pat. Nos. 4,649,911 and 4,119,096).

Typically, the lysozyme is administered in a pharmaceutically acceptable carrier. Such examples include saline solution, DMSO, an alcohol, or water. Such carriers are well known in the art, and the specific carriers employed may be varied depending upon factors such as size of the subject being treated, treatment dose, and the like.

Further, the time over which the lysozyme is administered may vary as is well known in the art to achieve the desired results. For example, the lysozyme may be administered as an aerosol from about 10 minutes to about 1 hour per treatment regimen, 3 times daily, or until the desired daily dosage is fully administered.

In addition, forms of lysozyme may be derived from the eggs of chickens and other species, or synthesized by a bioprocess, such as fermentation. All forms of lysozyme, regardless of source, would follow a treatment similar to that described above.

Figure 2:

Experimental Findings
Preferential Binding of Lysozyme to Elastic Fibers in Pulmonary Emphysema Emphysematous lungs showed a significant increase in extracellular immunostaining for lysozyme compared to either normal or fibrotic lung tissues (3.4±0.5(s.d.) vs 1.6±0.8 and 1.9±1.0, respectively; $p<0.05$; FIG. 1). In all three groups, there was preferential staining of interstitial, vascular, and pleural elastic fibers. However, the emphysematous lungs showed particularly intense staining of these fibers, especially in areas where there was airspace dilatation and attenuation of the alveolar septa. The immunostained elastic fibers associated with alveolar distention often appeared fragmented (FIG. 2).

Tissue sections from normal lungs, treated with bovine testicular hyaluronidase and incubated with egg-white lysozyme, showed a significant increase in immunostaining for lysozyme compared to controls not exposed to hyaluronidase (1.9±0.8 vs 1.2±0.7, respectively; $p<0.05$). This result was not due to increased immunostaining of endogenous lysozyme, since tissue sections treated with hyaluronidase, but not incubated with lysozyme, showed no significant increase in immunostaining compared to controls (0.9±0.2 vs 0.6±0.2, respectively; $p>0.05$).

The anti-human lysozyme antibody used in these studies reacted positively when tested against both human neutrophil lysozyme and egg-white lysozyme.

Attachment of Lysozyme to Elastic Fibers In Vitro

Lysozyme was tested for its ability to bind to elastic fibers in vitro, using a cell-free matrix preparation. The matrix was prepared from cultures of rat pleural mesothelial cells, which have previously been shown to synthesize elastin (15). Both the histochemical and immunofluorescence studies demonstrate that the matrix contains a complex network of elastic fibers. Relatively little collagen is present, based on the absence of positive (red) staining for this component with the Verhoeff-Van Gieson stain (5).

Figure 3:
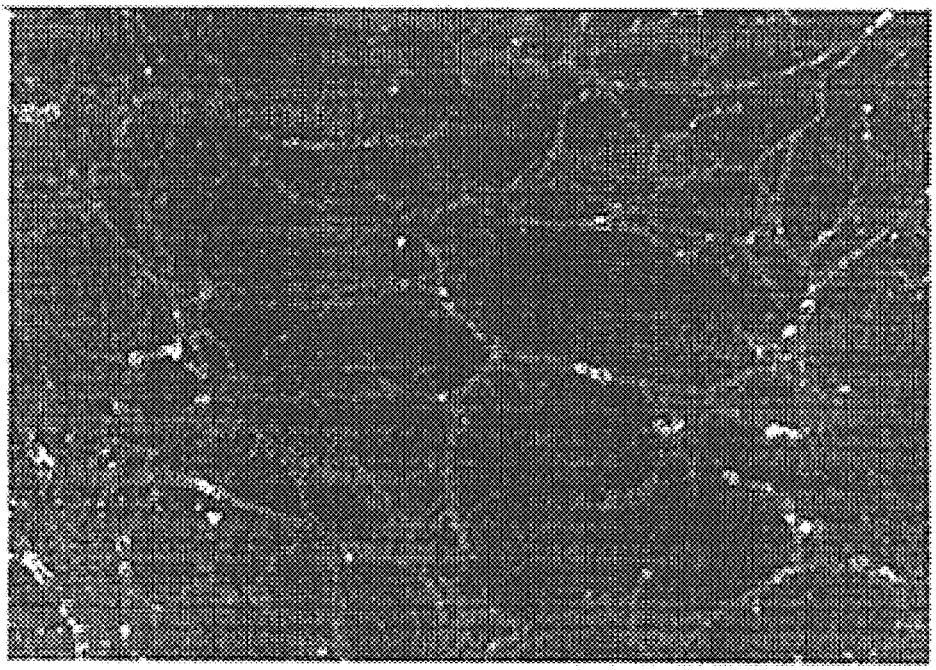

To determine if lysozyme binds to these fibers, matrix samples were incubated with a 0.1% solution of the protein for 30 min, washed, and subjected to immunofluorescence studies, using anti-lysozyme antibodies. The resulting pattern of fluorescence resembled the appearance of the matrix elastic fibers, indicating that lysozyme binds to these fibers (FIG. 3).

Figure 4:
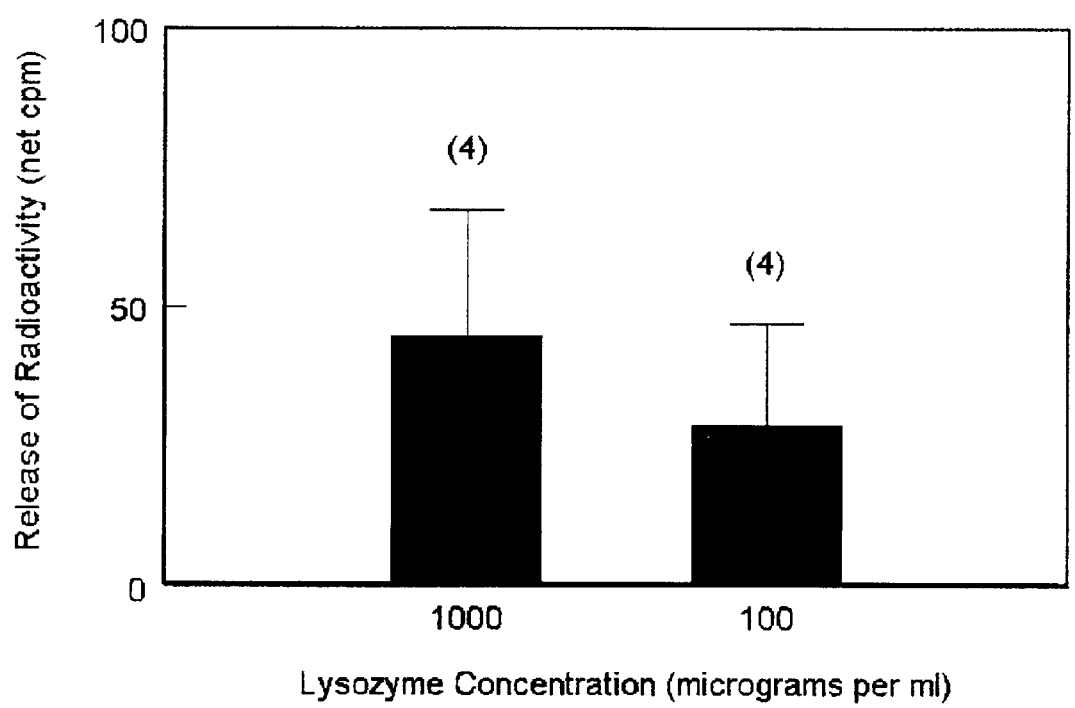

The ability of lysozyme to degrade elastic fibers was determined by exposing radiolabeled matrix to 1 mg/ml or 100 µg/ml of egg-white lysozyme for 3 hrs at 37° C. Such treatment produced no significant release of radioactivity, indicating that lysozyme does not cause elastolysis (FIG. 4).

Intratracheal Administration of Lysozyme

Syrian hamsters, weighing approximately 100 g, were placed inside the plexiglass chamber and exposed to aerosolized chicken egg-white lysozyme (20 mg in 20 ml water) for 50 min. Controls were exposed to 20 ml water alone for 50 minutes. The animals were sacrificed either 30 min or 24 hrs after exposure, and their lungs were fixed in situ by inserting a catheter into the trachea and instilling 10 percent neutral-buffered formalin at a pressure of 20 cm $H_2O$. After 2 hours, both the lungs and the heart were removed from the chest as a single block and additionally fixed in 10 percent formalin for several days. The lungs were then dissected free of extraparenchymal structures, sectioned randomly, and processed for histology. Unstained slide sections were treated with goat serum for 30 min, washed with PBS, then incubated with goat anti-rat lung elastin antiserum for 1 hr and washed with PBS. After treatment with rabbit serum for 30 min, a secondary, fluoresceinlabeled rabbit anti-goat IgG antibody was applied for 1 hr. The slide sections were then washed with PBS and examined with a fluorescence microscope. Additional sections were stained with hematoxylin and eosin to determine possible inflammatory changes in the lungs.

Figure 5:
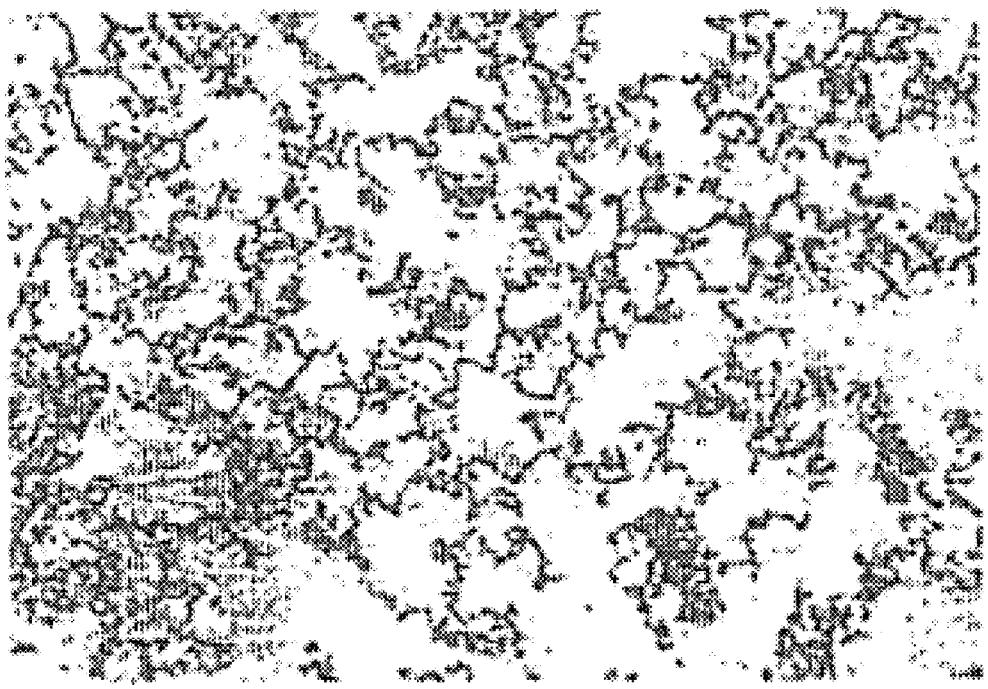
Figure 6:
Figure 6:

Hamsters exposed to aerosolized lysozyme for 50 minutes showed no inflammation at 24 hrs (FIG. 5). Immunofluorescence studies, using anti-lysozyme antibodies, demonstrated that the exogenous lysozyme was present in the pulmonary interstitium 30 minutes after completion of the aerosol exposure and could still be detected at 24 hrs (FIG. 6).

Discussion of Findings

The results of these experiments indicate that lysozyme binds to elastic fibers but does not cause either elastic fiber injury in vitro or lung injury in vivo. Lysozyme may therefore be a safe and effective agent for the treatment of lung diseases involving infection and/or damage to elastic fibers. The ability of lysozyme to bind to elastic fibers, readily penetrate lung tissues following aerosolization, and remain in the lung for at least 24 hrs strongly suggests that this protein could also act as a vehicle to reduce the clearance of intratracheally instilled agents from the lung. Furthermore, the attachment of lysozyme to polyanionic compounds associated with mucus, such as hyaluronan, may serve to disaggregate impacted secretions within airways, thus improving respiration in diseases such as pneumonia, bronchiectasis, and cystic fibrosis.

References

1. Agerberth B, Grunewald J, Castanos-Velez E, Olsson B, Jornvall H, Wigzell H, Eklund A, Gudmundsson G H. Antibacterial components in bronchoalveolar lavage fluid from healthy individuals and sarcoidosis patients. Am J Respir Crit Care Med 1999 July;160(1):283–90.
2. Travis S M, Conway B A, Zabner J, Smith J J, Anderson N N, Singh P K, Greenberg E P, Welsh M J. Activity of abundant antimicrobials of the human airway. Am J Respir Cell Mol Biol 1999 May;20(5):872–9.
3. Schnapp D, Harris A. Antibacterial peptides in bronchoalveolar lavage fluid. Am J Respir Cell Mol Biol 1998 September;19(3):352–6.
4. Shteyngart B, Chaiwiriyakul S, Wong J, Cantor J O. Preferential binding of lysozyme to elastic fibers in pulmonary emphysema. Thorax 53:193–196, 1998.
5. Cantor J O, Cerreta J M, Armand G, Turino G M. Further investigation of the use of intratracheally administered hyaluronan to ameliorate elastase-induced emphysema. Exp Lung Res 1997; 23:229–44.
6. Baccarani-Contri M, Vincenzi D, Cicchetti F, Mori G, Pasquali-Ronchetti I. Immunocytochemical localization of proteoglycans within normal elastin fibers. Eur J Cell Biol 1990;53:305–12.
7. Baccarani-Contri M, Fomieri C, Pasquali-Ronchetti I. Elastin-proteoglycans association revealed by cytochemical methods. Conn Tissue Res 13:237–249, 1985.
8. Amaya J. The effect of steroids on organ-cultured porcine trabecular meshwork: an ultrastructural, biochemical, and lectin histochemical study. Acta Societatis Opthalmologicae Japonicae 1995;99:995–1004.
9. Park P W, Diedermann K, Mecham L, Bissett D L, Mecham R P. Lysozyme binds to elastin and protects elastin from elastase-mediated dgradation. J Invest Dermatol 1996;106:1075–1080.
10. Lee-Huang S, Huang P L, Sun Y, Huang P L, Kung H F, Blithe D L, Chen H C. Lysozyme and RNases as anti-HIV components in beta-core preparations of human chorionic gonadotropin. Proc Natl Acad Sci USA 1999;96:2678–81.
11. Van Damme M P, Moss J M, Murphy W H, Preston B N. Binding properties of glycosaminoglycans to lysozyme-effect of salt and molecular weight. Arch Biochem Biophys 1994;310:16–24.
12. Zhao H W, Lu C J, Yu R J, Hou X M. An increase in hyaluronan by lung fibroblasts: a biomarker for intensity and activity of interstitial pulmonary fibrosis? Respirology 1999; 4(2):131–8.
13. Gerdin B, Haligren R. Dynamic role of hyaluronan (HYA) in connective tissue activation and inflammation. J Intern Med 1997;242(1):49–55.
14. Cantor J O, Cerreta J M, Osman M, Mott S H, Mandl I, Turino G M. Glycosaminoglycan synthesis in bleomycin-induced pulmonary fibrosis: Biochemistry and autoradiography. Proc Soc Exp Biol Med 1983;174:172–181.
15. Cantor J O, Wilihite M, Bray B A, Keller S, Mandl I, Turino G M. Synthesis of crosslinked elastin by a mesothelial cell culture. Proc Soc Exp Biol Med 1986;81:387–391.

What is claimed is:

1. A method of treating pneumonia in a mammal that suffers from pneumonia that consists of intratracheally administering to the lung of the mammal a therapeutically effective amount of lysozyme as the sole active ingredient in the treatment of the mammal suffering from pneumonia.

2. A method of claim 1, wherein the intratracheal administration is performed by nebulization.

3. A method of claim 1, wherein the lysozyme is isolated from a natural source, such as eggs.

4. A method of claim 1, wherein the lysozyme is produced by a bioprocess, such as fermentation.

5. A method of claim 1, wherein the mammal is a human.

6. A method of claim 1, wherein the pneumonia is due to viruses, bacteria, or fungi, including pneumonias related to HIV-induced immunodeficiency.

7. A method of claim 1, wherein the lysozyme is administered with a carrier, such as DMSO, an alcohol, or water.

8. A method of claim 1, wherein the effective amount of lysozyme is from about 10 micrograms per kilogram body weight per day to about 1 milligram per kilogram body weight per day.

* * * * *